United States Patent
Hagiwara

(10) Patent No.: US 8,989,470 B2
(45) Date of Patent: Mar. 24, 2015

(54) IMAGE PROCESSING APPARATUS, PROGRAM AND IMAGE DIAGNOSTIC APPARATUS FOR HIGH-FREQUENCY ENHANCEMENT PROCESSING

(75) Inventor: Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 113 days.

(21) Appl. No.: 13/403,093

(22) Filed: Feb. 23, 2012

(65) Prior Publication Data

US 2012/0219199 A1 Aug. 30, 2012
US 2013/0101195 A9 Apr. 25, 2013

(30) Foreign Application Priority Data

Feb. 26, 2011 (JP) ................................. 2011-040984

(51) Int. Cl.
- G06K 9/00 (2006.01)
- A61B 6/03 (2006.01)
- G06T 5/00 (2006.01)
- A61B 6/00 (2006.01)

(52) U.S. Cl.
CPC .............. A61B 6/032 (2013.01); *A61B 6/037* (2013.01); *A61B 6/4417* (2013.01); A61B 6/466 (2013.01); *A61B 6/504* (2013.01); A61B 6/5211 (2013.01); *A61B 6/5258* (2013.01); G06T 5/003 (2013.01); *G06T 2207/10081* (2013.01); *G06T 2207/20192* (2013.01)
USPC ....................................................... 382/131

(58) Field of Classification Search
None
See application file for complete search history.

(56) References Cited

U.S. PATENT DOCUMENTS

| | | | | |
|---|---|---|---|---|
| 4,739,481 A | * | 4/1988 | Yoshitome | 600/425 |
| 5,345,513 A | * | 9/1994 | Takeda et al. | 382/132 |
| 6,295,331 B1 | * | 9/2001 | Hsieh | 378/19 |
| 6,410,921 B1 | * | 6/2002 | Nakazawa | 250/370.09 |
| 6,754,398 B1 | * | 6/2004 | Yamada | 382/260 |
| 6,771,793 B1 | * | 8/2004 | Yamada | 382/264 |
| 6,950,494 B2 | | 9/2005 | Vija et al. | |
| 7,274,770 B2 | | 9/2007 | Nederpelt | |
| 2002/0067862 A1 | * | 6/2002 | Kim | 382/266 |
| 2005/0254721 A1 | | 11/2005 | Hagiwara | |

(Continued)

FOREIGN PATENT DOCUMENTS

| | | | | |
|---|---|---|---|---|
| JP | 2004073432 | | 3/2004 | |
| JP | 2004283410 A | * | 10/2004 | A61B 6/00 |

OTHER PUBLICATIONS

Translated Version of JP 2004-283410, pp. 1-44.*

Primary Examiner — Sumati Lefkowitz
Assistant Examiner — Carol Wang
(74) Attorney, Agent, or Firm — Armstrong Teasdale LLP

(57) ABSTRACT

An image processing apparatus is provided. The image processing apparatus includes an acquiring device configured to acquire a typical pixel value corresponding to a noted region in an image, a calculating device configured to calculated index values of variances in pixel values in the noted region or in both the noted region and a region adjacent to the noted region, a first enhancement degree determination device configured to determine an enhancement degree according to the acquired typical pixel value and each of the calculated index values, and an image processing device configured to perform high-frequency enhancement processing on the noted region, based on the enhancement degree determined by the first enhancement degree determination device.

18 Claims, 9 Drawing Sheets

(56) References Cited

U.S. PATENT DOCUMENTS

2007/0172104 A1* 7/2007 Nishide et al. ............... 382/131
2009/0136110 A1 5/2009 Kaji
2009/0238408 A1* 9/2009 Ikeda et al. ................... 382/103

* cited by examiner

IMAGE PROCESSING APPARATUS, PROGRAM AND IMAGE DIAGNOSTIC APPARATUS FOR HIGH-FREQUENCY ENHANCEMENT PROCESSING

CROSS REFERENCE TO RELATED APPLICATIONS

This application claims the benefit of Japanese Patent Application No. 2011-040984 filed Feb. 26, 2011, which is hereby incorporated by reference in its entirety.

BACKGROUND OF THE INVENTION

The present invention relates to an image processing apparatus, a program and an image diagnostic apparatus which improve spatial resolution of an image.

Conventionally, in many X-ray CT (Computed Tomography) apparatuses, an arithmetic operation for overlay with a reconstruction function is performed on projection data acquired by imaging, and back projection processing is executed thereon to thereby reconstruct an X-ray CT image.

The quality of the X-ray CT image depends on the characteristic of the reconstruction function used in image reconstruction. Therefore, in each X-ray CT apparatus, a plurality of types of reconstruction functions respectively different in the quality of the reconstructed image are prepared and provided to a user. There are prepared, for example, a lung field function close to high spatial resolution so adjusted that a high-frequency component appears relatively strongly, a soft part function close to low noise so adjusted that a high-frequency component appears relatively weakly, a standard function having an intermediate property between these, etc. The user properly uses these reconstruction functions according to diagnostic purposes, sections to be observed and the like. See, for example, paragraphs [0021], [0029] and [0030] of Japanese Patent Application Laid-Open No. 2004-073432.

On the other hand, when an image is reconstructed using a reconstruction function, spatial resolution and noise level in the reconstructed image are in a trade off relationship with respect to each other. Therefore, when such a reconstruction function that the high-frequency component appears extremely strongly is used in an attempt to enhance the spatial resolution to the maximum, an increase in noise becomes sharp so that the image may result in an image that does not withstand a practical use.

With this situation, in regard to the previously-prepared reconstruction function, the balance between spatial resolution and a noise level has been adjusted within a range durable for practical use. Therefore, even in the case of the reconstruction function close to the highest spatial resolution, potential spatial resolution of projection data has not yet been drawn to a maximal degree.

On the other hand, a section (e.g., auditory ossicles or the like) having a very fine structure even within the sections of a subject has been desired at a higher spatial resolution. There has been room for further high spatial resolution. However, when using the reconstruction function adjusted such that an improvement in spatial resolution is pursued at random, and such that the high-frequency component appears strongly, noise is increased needlessly with respect to a region that does not require such a high spatial resolution (e.g., a soft tissue region), thus leading to an undesirable result.

With the foregoing in view, a process capable of making a further improvement in spatial resolution for the region without increasing noise needlessly is desired.

SUMMARY OF THE INVENTION

In a first aspect, an image processing apparatus is provided. The image processing apparatus includes an acquiring device which acquires a typical pixel value corresponding to a noted region in an image, a calculating device which calculates index values of variances in pixel values in the noted region or the noted region and an adjacent region thereof, a first enhancement degree determination device which determines an enhancement degree according to the acquired typical pixel value and each of the calculated index values, and an image processing device which performs high-frequency enhancement processing on the noted region, based on the enhancement degree determined by the first enhancement degree determination device.

In a second aspect the image processing apparatus according to the first aspect is provided, wherein the first enhancement degree determination device specifies an enhancement degree corresponding to each of the calculated index values, based on a first relation that indicates a relation between each of the index values of the variances and the enhancement degree and varies according to the typical pixel value corresponding to the noted region.

Incidentally, the first enhancement degree determination device determines the first relation according to a typical pixel value. It partly includes such a case that a plurality of different typical pixel values and the same relation are associated with each other.

In a third aspect, the image processing apparatus according to the second aspect is provided, wherein in the first relation, each of index values of variances included in a first range and a first enhancement degree are associated with each other, each of index values of variances included in a second range larger in index value than the first range and a second enhancement degree smaller than the first enhancement degree are associated with each other, and each of index values of variances included in a third range larger in index value than the second range and a third enhancement degree larger than the second enhancement degree are associated with each other.

In a fourth aspect, the image processing apparatus according to the third aspect is provided, wherein the second range is a range of index values of variances corresponding to the existence of an artifact.

In a fifth aspect, the image processing apparatus according to any one of the first to fourth aspects is provided, further including second enhancement determination device which determines an enhancement degree according to the acquired typical pixel value, wherein the image processing device performs high-frequency enhancement processing on the noted region, based on the enhancement degree determined by the second enhancement degree determination device.

In a sixth aspect, the image processing apparatus according to the fifth aspect is provided, wherein the second enhancement degree determination device specifies an enhancement degree corresponding to the acquired typical pixel value, based on a second relation indicative of a relation between a typical pixel value corresponding to the noted region and an enhancement degree.

In a seventh aspect, the image processing apparatus according to the sixth aspect is provided, wherein in the second relation, a typical pixel value included in a fourth range and a fourth enhancement degree are associated with each other, a typical pixel value included in a fifth range larger in pixel value than the fourth range and a fifth enhancement degree than the fourth enhancement degree are associated with each other, a typical pixel value included in a sixth range larger in pixel value than the fifth range and a sixth enhancement degree smaller than the fifth enhancement degree are associated with each other, and a typical pixel value included in a seventh range larger in pixel value than the sixth range and a seventh enhancement degree larger than the sixth enhancement degree are associated with each other.

In an eighth aspect, the image processing apparatus according to the seventh aspect is provided, wherein the fourth range is a range of pixel values corresponding to the existence of air, and the sixth range is a range of pixel values corresponding to the existence of a soft tissue.

In a ninth aspect, the image processing apparatus according to any one of the sixth to eighth aspects is provided, wherein the image is an X-ray CT image, and wherein the second enhancement degree determination device determines an enhancement degree, based on the second relation that varies according to a reconstruction function used in reconstruction of the X-ray CT image.

Incidentally, the second enhancement degree determination device determines the second relation according to a reconstruction function. It partly includes such a case that a plurality of different reconstruction functions and the same relation are associated with each other.

In a tenth aspect, the image processing apparatus according to any one of the first to ninth aspects is provided, further including third enhancement degree determination device which determines an enhancement degree in such a manner that a larger value is acquired when an edge is not detected by edge detection processing on the noted region or the noted region and an adjacent region thereof rather than when the edge is detected by the edge detection processing, wherein the image processing device performs high-frequency enhancement processing on the noted region, based on the enhancement degree determined by the third enhancement degree determination device.

In an eleventh aspect, the image processing apparatus according to the tenth aspect is provided, wherein the edge detection processing is a process for determining that the edge has been detected where the number of pixels, at which a difference between each of pixels values of pixels in regions adjacent to the noted region and a typical pixel value corresponding to the noted region is greater than or equal to a predetermined threshold value, of the pixels in the regions adjacent to the noted region, is greater than or equal to a predetermined number.

In a twelfth aspect, the image processing apparatus according to any one of the first to eleventh aspects is provided, wherein the image is an X-ray CT image, wherein the image processing apparatus further includes fourth enhancement degree determination device which determines an enhancement degree in such a manner that a large value is acquired as the distance from the center of reconstruction of the X-ray CT image to the noted region increases, and wherein the image processing device performs high-frequency enhancement processing on the noted region, based on the enhancement degree determined by the fourth enhancement degree determination device.

In a thirteenth aspect, the image processing apparatus according to any one of the fifth to twelfth aspects is provided, wherein the image processing device performs high-frequency enhancement processing on the noted region in accordance with enhancement degrees obtained by performing multiplication, addition or weighted addition on a plurality of the enhancement degrees determined.

In a fourteenth aspect, the image processing apparatus according to any one of the first to thirteenth aspects is provided, wherein the high-frequency enhancement processing is sharpening filter processing.

In a fifteenth aspect, the image processing apparatus according to any one of the first to fourteenth aspects is provided, wherein the typical pixel value corresponding to the noted region is a pixel value of a central pixel in the noted region, an average value of pixel values in the noted region or both the noted region and the adjacent region thereof, or a weighted average value thereof.

In a sixteenth aspect, the image processing apparatus according to any one of the first to fifteenth aspects is provided, wherein each of the index values of the variances is a variance or standard deviation of pixel values in the noted region or the noted region and its adjacent region.

In a seventeenth aspect, a program is provided. The program is for causing a computer to function as an acquiring device which acquires a typical pixel value corresponding to a noted region in an image, a calculating device which calculates index values of variances in pixel values in the noted region or the noted region and an adjacent region thereof, a first enhancement degree determination device which determines an enhancement degree according to the acquired typical pixel value and each of the calculated index values, and an image processing device which performs high-frequency enhancement processing on the noted region, based on the enhancement degree determined by the first enhancement degree determination device.

In an eighteenth aspect, an image diagnostic apparatus is provided. The image diagnostic apparatus is equipped with an acquiring device which acquires a typical pixel value corresponding to a noted region in an image, a calculating device which calculates index values of variances in pixel values in the noted region or the noted region and an adjacent region thereof, a first enhancement degree determination device which determines an enhancement degree according to the acquired typical pixel value and each of the calculated index values, and an image processing device which performs high-frequency enhancement processing on the noted region, based on the enhancement degree determined by the first enhancement degree determination device.

In a nineteenth aspect, the image diagnostic apparatus according to the eighteenth aspect is provided, wherein X-ray CT imaging is conducted to reconstruct an image.

According to the aspects described above, spatial resolution can be improved with respect to a region desirous of high spatial resolution without increasing noise needlessly.

DETAILED DESCRIPTION OF THE INVENTION

Exemplary embodiments will be explained herein.

Figure 1:
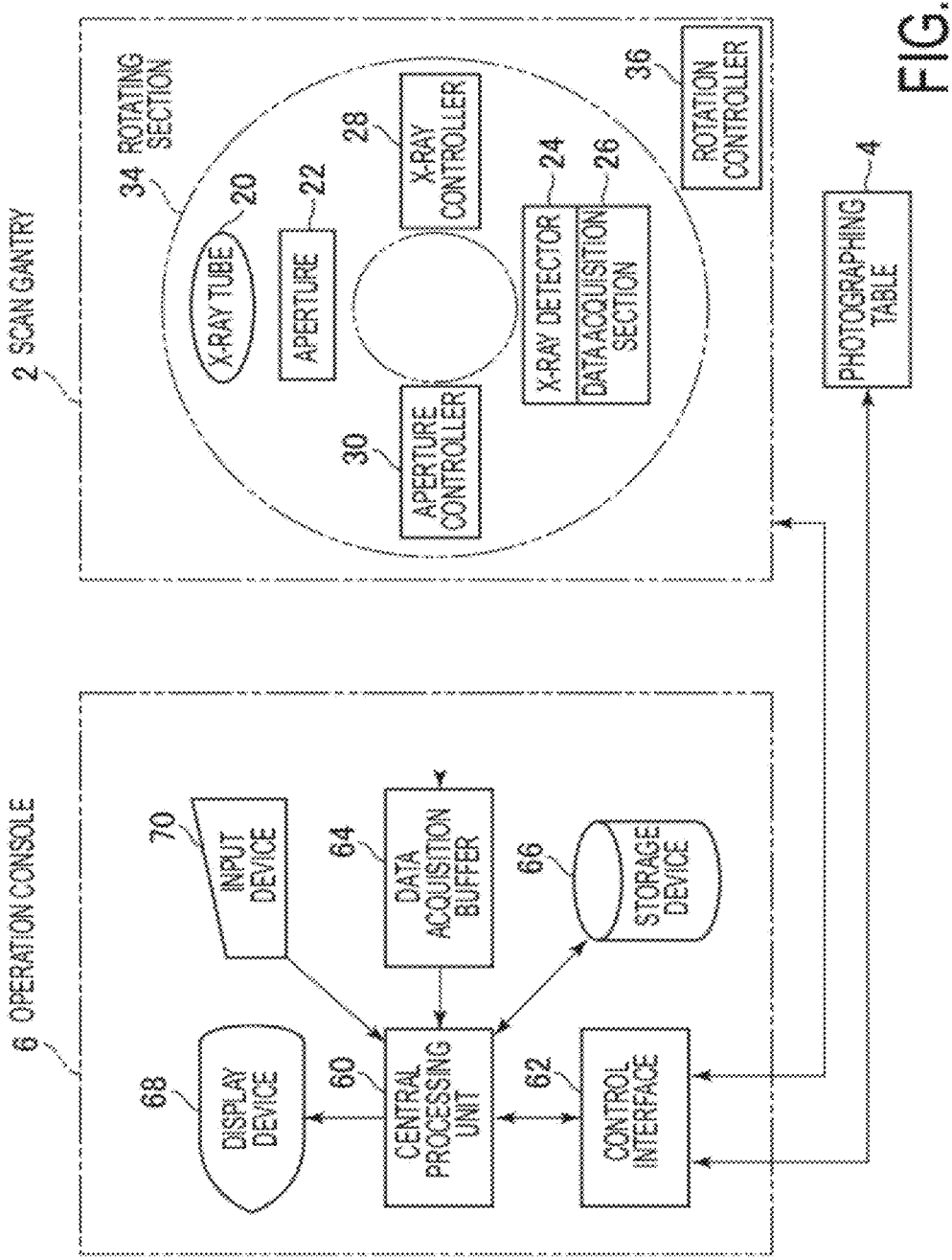
FIG. 1 is a diagram schematically showing a configuration of an X-ray CT apparatus.

FIG. 1 is a diagram schematically showing a configuration of an X-ray CT apparatus.

As shown in FIG. 1, the present X-ray CT apparatus is equipped with a gantry 2, a photographing table 4 and an operation console 6. The gantry 2 has an X-ray tube 20. X-rays (not shown) emitted from the X-ray tube 20 are formed to be an X-ray beam such as a sectorial fan beam, a cone beam or the like by means of an aperture 22 and applied to an X-ray detector 24.

The X-ray detector 24 has a plurality of X-ray detecting elements arranged on a two-dimensional basis as viewed in an extending direction (channel direction) of the sectorial X-ray beam and its thickness direction (row direction).

A data acquisition section 26 is connected to the X-ray detector 24. The data acquisition section 26 acquires data detected by the individual X-ray detecting elements of the X-ray detector 24 as projection data. The application of the X-rays from the X-ray tube 20 is controlled by an X-ray controller 28. Incidentally, the relationship of connection between the X-ray tube 20 and the X-ray controller 28 is omitted from the drawing.

Data about a tube voltage and current supplied to the X-ray tube 20 by the X-ray controller 28 are acquired by the data acquisition section 26. Incidentally, the relationship of connection between the X-ray controller 28 and the data acquisition section 26 is omitted from the drawing.

The aperture 22 is controlled by an aperture controller 30. Incidentally, the relationship of connection between the aperture 22 and the aperture controller 30 is omitted from the drawing.

A rotating section 34 of the gantry 2 is equipped with components from the X-ray tube 20 to the aperture controller 30. The rotation of the rotating section 34 is controlled by a rotation controller 36. Incidentally, the relationship of connection between the rotating section 34 and the rotation controller 36 is omitted from the drawing.

The photographing table 4 carries an unillustrated subject in an X-ray irradiation space of the gantry 2 and carries the same out of the X-ray irradiation space.

The operation console 6 has a central processing unit 60. The central processing unit 60 is configured by, for example, a computer or the like. A control interface 62 is connected to the central processing unit 60. The gantry 2 and the photographing table 4 are connected to the control interface 62. The central processing unit 60 controls the gantry 2 and the photographing table 4 through the control interface 62.

The data acquisition section 26, the X-ray controller 28, the aperture controller 30 and the rotation controller 36 in the gantry 2 are controlled through the control interface 62. Incidentally, the individual connections between those parts and the control interface 62 are omitted from the drawing.

A data acquisition buffer 64 is connected to the central processing unit 60. The data acquisition section 26 of the gantry 2 is connected to the data acquisition buffer 64. Data acquired by the data acquisition section 26 are inputted to the central processing unit 60 through the data acquisition buffer 64.

The central processing unit 60 performs a scan planning process of an actual scan according to the operations by an operator. Also the central processing unit 60 performs image reconstruction using projection data of a plurality of views acquired through the data acquisition buffer 64. A three-dimensional image reconstruction process or the like by, for example, a filtered back projection method is used in the image reconstruction. The operator is able to select a reconstruction function, so-called kernel used in image reconstruction according to a region or section to be observed and purposes. As the reconstruction function, a standard function, a soft part region function, a high resolution function and so on have been prepared.

The central processing unit 60 also performs adaptive high-frequency enhancement processing to improve spatial resolution of an X-ray CT image which is a reconstructed image.

A storage device 66 is connected to the central processing unit 60. The storage device 66 stores therein various data, reconstructed images and a program or the like for implementing the function of the present X-ray CT apparatus.

A display device 68 and an input device 70 are respectively connected to the central processing unit 60. The display device 68 displays the reconstructed image and other information outputted from the central processing unit 60. The input device 70 is operated by the operator and inputs various instructions, information and the like to the central processing unit 60. The operator interactively operates the present X-ray CT apparatus by use of the display device 68 and the input device 70.

Figure 2:
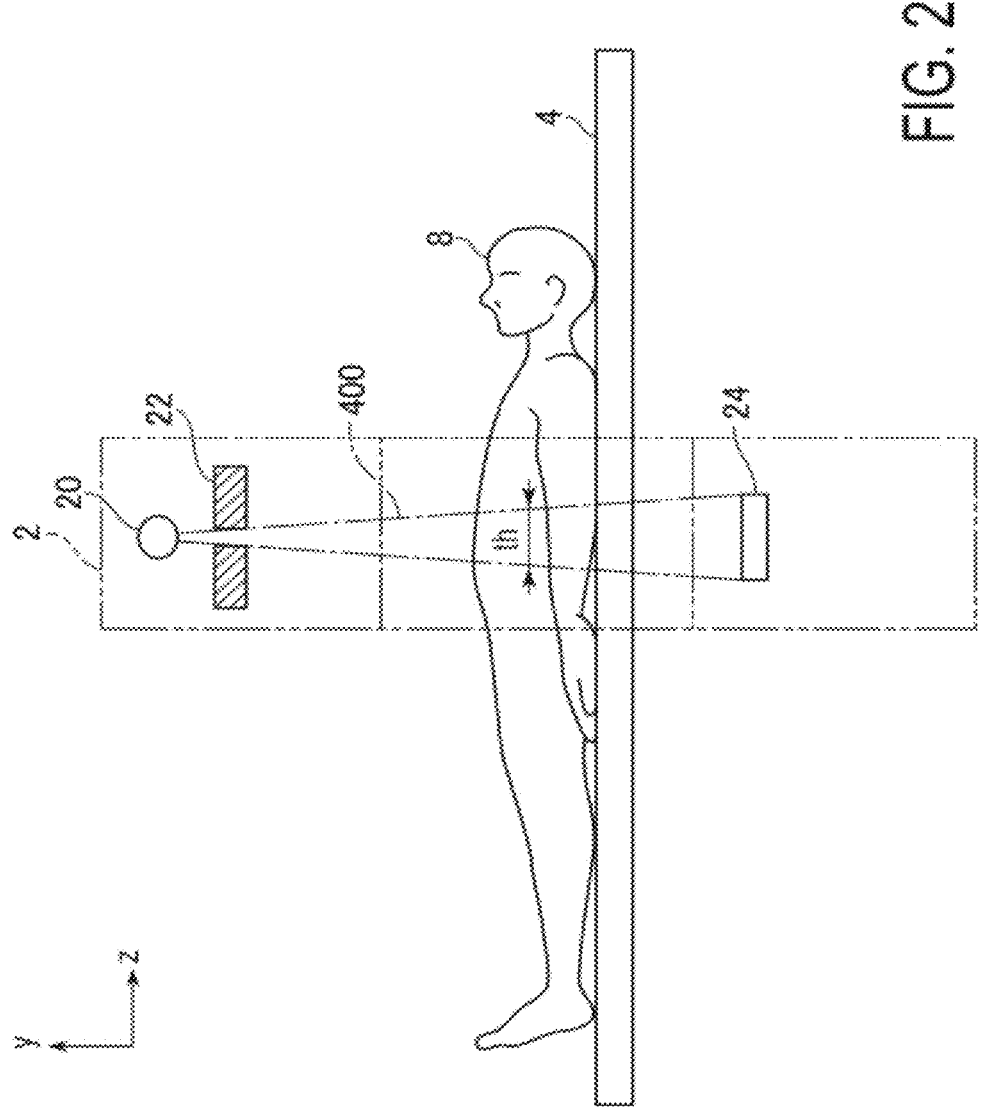
FIG. 2 is a diagram of a gantry as viewed from its side surface.

FIG. 2 is a diagram of the gantry 2 as viewed from its side surface. As shown in FIG. 2, an X-ray radiated from the X-ray tube 20 is shaped to be a fan-shaped X-ray beam 400 through the aperture 22 and applied to the X-ray detector 24. The subject 8 placed on the photographing table 4 with its body axis being allowed to intersect with the sectorial plane of such an X-ray beam 400, is carried in its corresponding X-ray irradiation space.

The X-ray irradiation space is shaped in space lying inside the cylindrical structure of the gantry 2. An image of the subject 8 sliced by the X-ray beam 400 is projected onto the X-ray detector 24. The X-ray penetrated through the subject 8 is detected by the X-ray detector 24. The thickness th of the X-ray beam 400 applied to the subject 8 is adjusted according to the degree of opening of the aperture 22.

The X-ray tube 20, the aperture 22 and the X-ray detector 24 are rotated about the body axis of the subject 8 while maintaining the mutual relationship between them. Projection data about plural views per scan, e.g., 1000 views or so are acquired. The acquisition of the projection data is performed by a system of the X-ray detector 2, data acquisition section 26 and data acquisition buffer 64.

The central processing unit 60 performs image reconstruction of a tomographic image, based on the projection data acquired by the data acquisition buffer 64.

Incidentally, the direction of the body axis of the subject 8, i.e., the direction of conveyance of the subject 8 on the photographing table 4 is assumed to be a z direction as shown in FIG. 2 herein. Further, the vertical direction is assumed to be a y direction, and the horizontal direction perpendicular to the y and z directions is assumed to be an x direction.

Thus, the adaptive high-frequency enhancement processing of the X-ray CT image will now be explained.

Figure 3:
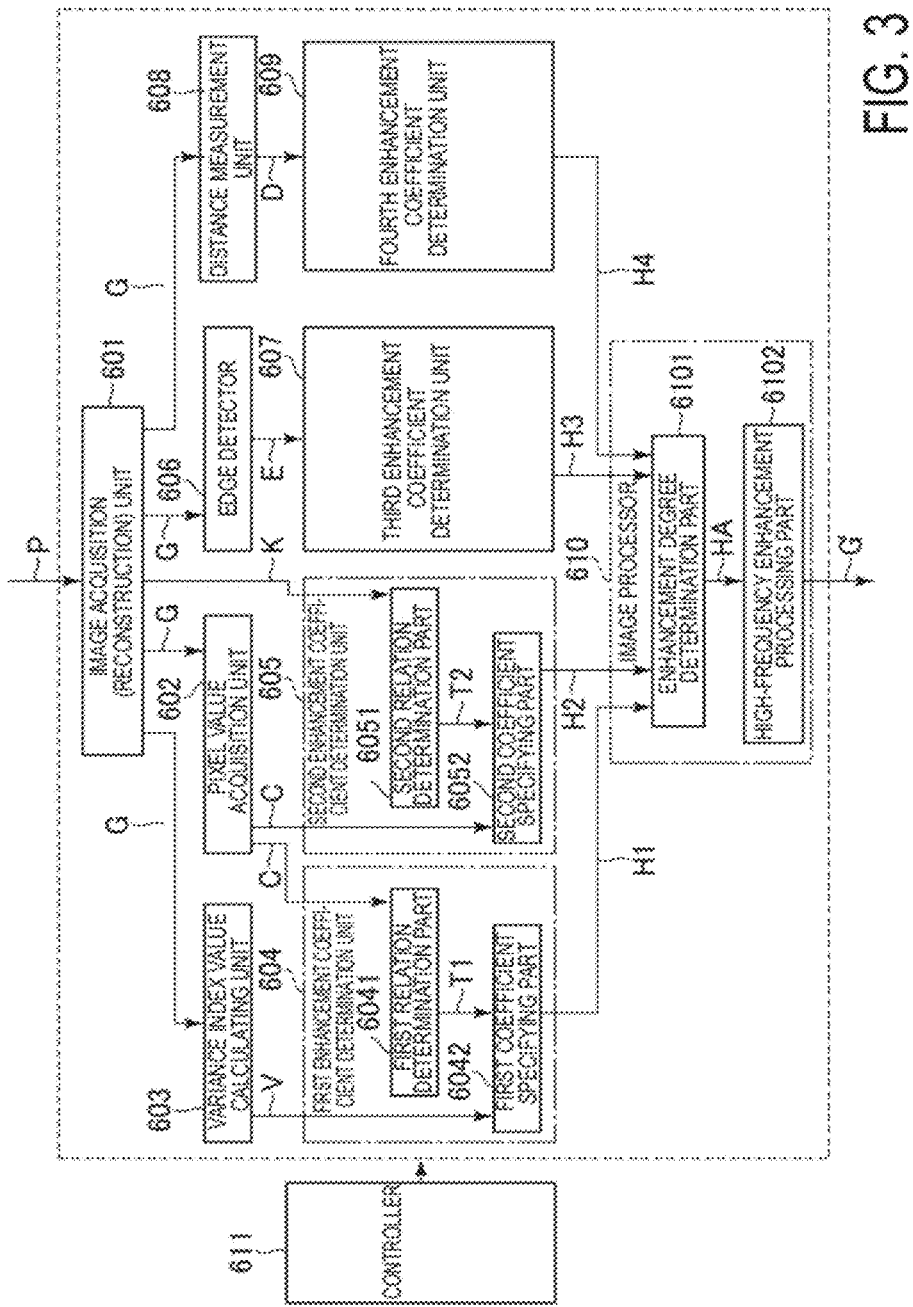
FIG. 3 is a functional block diagram of a portion related to adaptive high-frequency enhancement processing in the X-ray CT apparatus.
Figure 4:
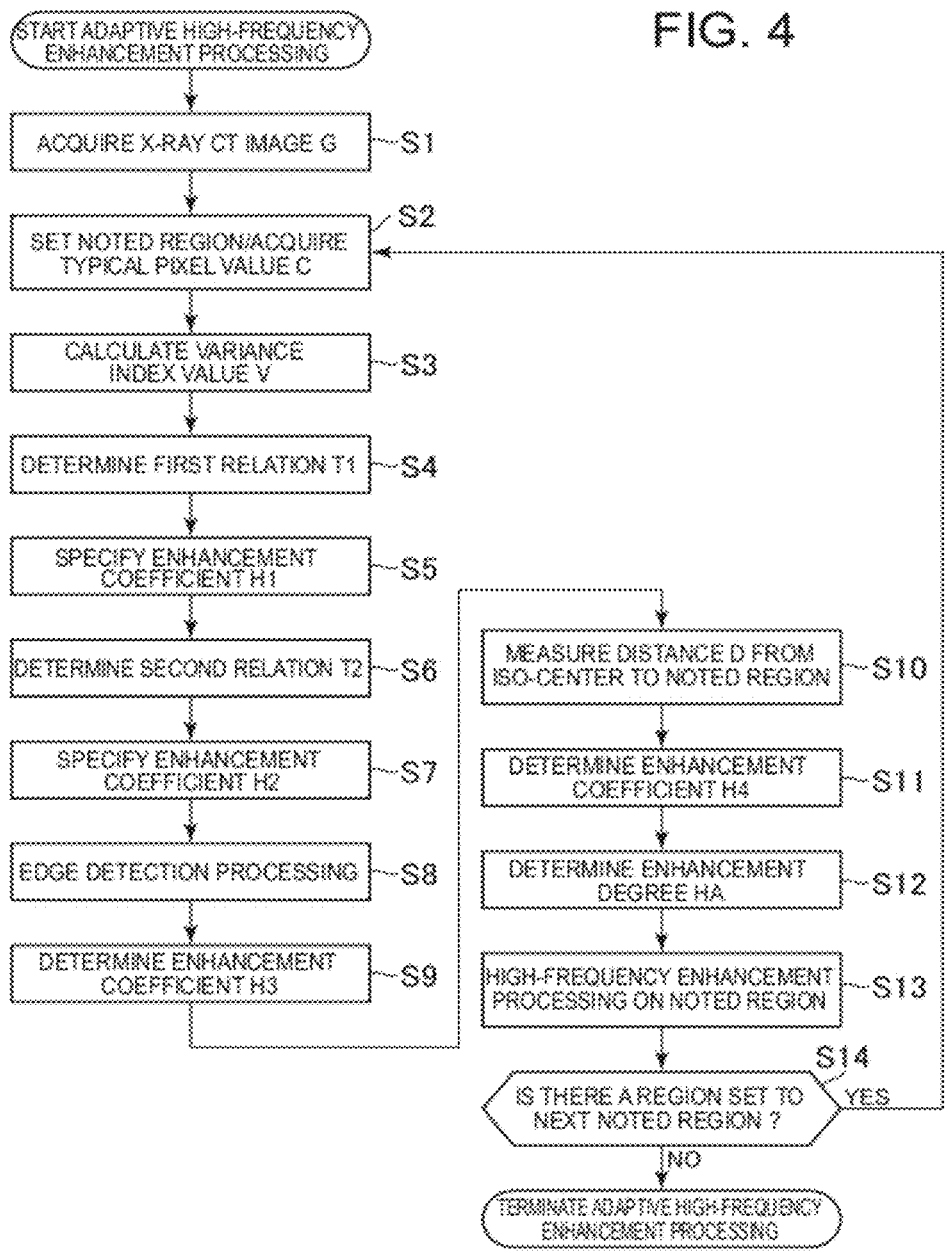
FIG. 4 is a flowchart of the adaptive high-frequency enhancement processing in the X-ray CT apparatus.

FIG. 3 is a functional block diagram of a section related to the adaptive high-frequency enhancement processing of the X-ray CT image in the X-ray CT apparatus. FIG. 4 is a flowchart of the adaptive high-frequency enhancement processing of the X-ray CT image.

As shown in FIG. 3, the present X-ray CT apparatus is equipped with an image acquisition unit 601, a pixel value acquisition unit 602, a variance index value calculating unit 603, a first enhancement coefficient determination unit 604, a second enhancement coefficient determination unit 605, an edge detector 606, a third enhancement coefficient determination unit 607, a distance measurement unit 608, a fourth enhancement coefficient determination unit 609, an image processor 610 and a controller 611.

The first enhancement coefficient determination unit 604 is equipped with a first relation determination part 6041 and a first coefficient specifying part 6042. The second enhancement coefficient determination unit 605 is equipped with a second relation determination part 6051 and a second coefficient specifying part 6052. The image processor 610 is equipped with an enhancement degree determination part 6101 and a high-frequency enhancement processing part 6102.

Incidentally, the already-acquired projection data are assumed to have been stored in the storage device 66.

At step S1, the image acquisition unit 601 acquires an X-ray CT image G which is a reconstructed image. Here, the image acquisition unit 601 reads projection data P from the storage device 66 and performs image reconstruction using a reconstruction function selected by a user, based on the read projection data P to thereby acquire the corresponding X-ray CT image. As the reconstruction function, there are considered a plurality of types of reconstruction functions different in balance between spatial resolution and a noise level in the reconstructed image. As the reconstruction function, there are mentioned, for example, a lung field function close to high spatial resolution, a soft part function close to a low noise level, a standard function having an intermediate property between these, etc.

At step S2, the controller 611 sets a noted region including one or plural pixels in the X-ray CT image G, and the pixel value acquisition unit 602 acquires a typical pixel value C corresponding to the noted region.

It is possible to roughly discriminate whether the noted region is any tissue of air, lung, mediastinal space/liver, bone/contrasted blood vessels, etc., based on the typical pixel value C corresponding to the noted region.

As the typical pixel value C corresponding to the noted region, there are considered, for example, a pixel value of a central pixel in the noted region, an average value of pixel values in the noted region or both the noted region and its adjacent region or a weighted average value thereof, etc. Herein, the noted region is assumed to be a region corresponding to one pixel. This will be called a noted pixel. The typical pixel value corresponding to the noted region is assumed to be the average value of pixel values at the noted pixel and eight adjacent pixels lying orthogonally through the length and breadth of the noted pixel. Thus, information about each pixel value related to a section indicated by the noted region can be obtained while suppressing the effect of noise.

At step S3, the variance index value calculating unit 603 calculates an index value (hereinafter called a variance index value V) indicative of the degree of variance in the pixel values at the noted region and its adjacent region.

It is possible to recognize the fineness of the structure of the noted region, its noise level, etc., based on the variance index value V. For example, it is possible to roughly grasp whether the noted region is any of (1) a soft part region of mediastinal space/liver or the like, (2) an artifact such as streak or the like and (3) so-called high-contrast region of lung/bone/contrasted blood vessels or the like.

As the variance index value V, there can be considered, for example, a variance or standard deviation of pixel values in the noted region or the noted region and its adjacent region, etc. Here, the variance index value V is assumed to be a standard deviation of pixel values at a predetermined matrix region centering on a noted pixel, for example, a region of 5×5 pixels.

At step S4, the first relation determination part 6041 determines a first relation T1 indicative of a relationship between a variance index value V and an enhancement coefficient H1, based on the typical pixel value C acquired at step S2. Incidentally, details on the first relation T1 and its determination method will be described later.

At step S5, the first coefficient specifying part 6042 specifies an enhancement coefficient H1 corresponding to the variance index value V calculated at step S3, by referring to the first relation T1 determined at step S4.

Here, the term enhancement coefficient is a coefficient used to determine or fix up the degree of enhancement of high-frequency enhancement processing performed on the noted region. The enhancement coefficient acts so as to relatively increase the degree of enhancement as the value thereof becomes large, and acts so as to relatively decrease the degree of enhancement as the value thereof becomes small.

Incidentally, as the method for determining the first relation T1, there is considered, for example, a method for dividing values each taken as the typical pixel value C corresponding to the noted region into a plurality of ranges, storing candidates for the first relation T1 in correspondence with one another every range and specifying the first relation T1 which is a candidate corresponding to the typical pixel value C acquired at step S2. For example, a predetermined function is prepared in which the typical pixel value C corresponding to the noted region is defined as a parameter. Then the typical pixel value C acquired at step S2 may be input to the predetermined function so as to derive the first function T1 therefrom.

Figure 5:
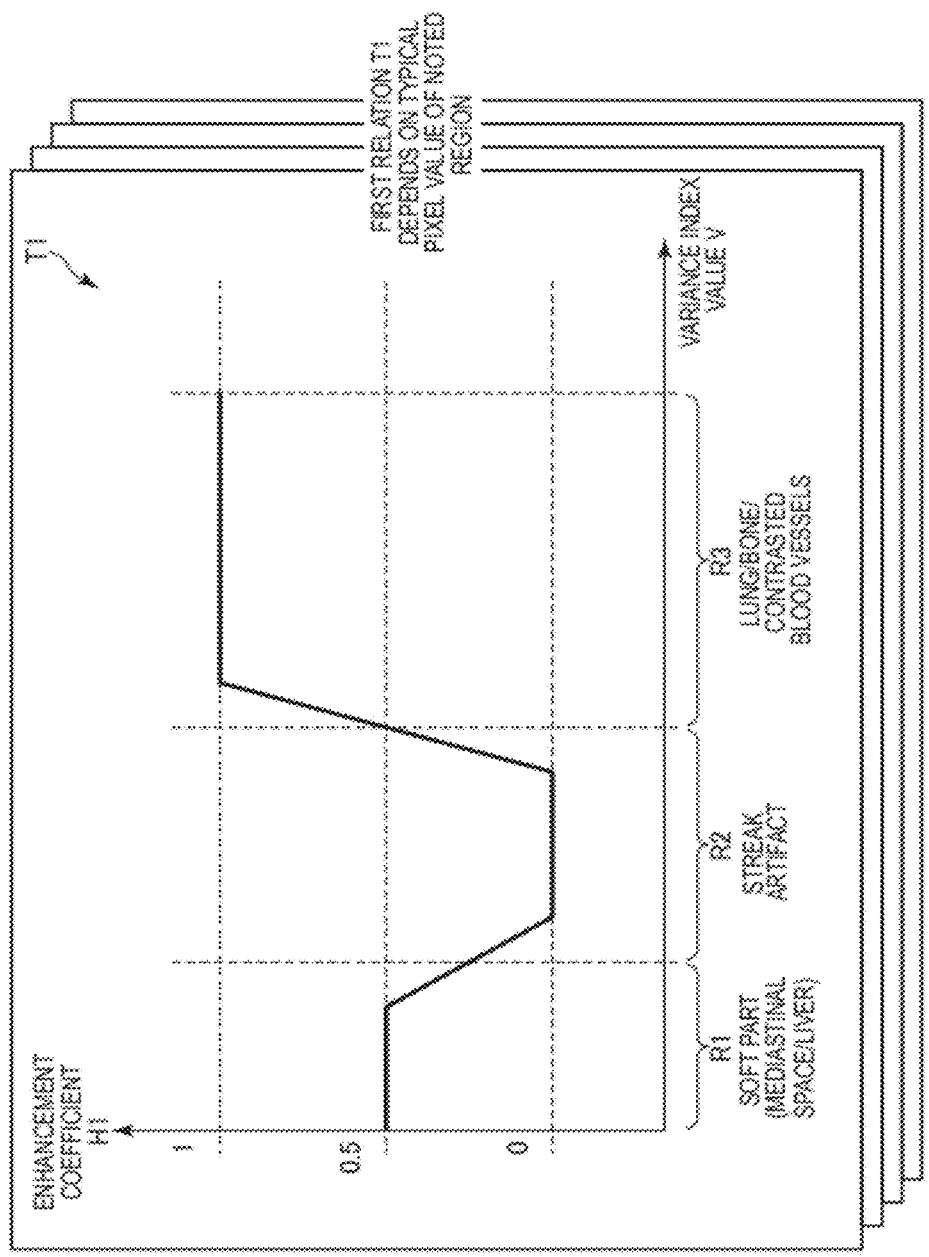
FIG. 5 is a diagram showing one example of a first relation indicative of a correlation between a variance index value and an enhancement coefficient.

One example of the first relation is shown in FIG. 5.

When the variance index value V is within a first range R1 relatively low in the variance index value V in the first relation T1 according to this example as shown in FIG. 5, there is a high possibility that the noted region will be on a structure near a flat. Therefore, an improvement in spatial resolution and noise suppression are balanced to share equally, so that the enhancement coefficient H1 is brought to 0.5 or so (first enhancement coefficient) corresponding to an intermediate level. When the variance index value V is within a second range R2 middle in the variance index value V, there is a high possibility that the noted region will be on a streak artifact. Therefore, the enhancement coefficient H1 is lowered to near zero indicative of the minimum level (second enhancement coefficient) so as to prevent the artifact from being enhanced. When the variance index value V is within a third range R3 relatively high in the variance index value V, there is a high possibility that the noted region will be on a fine structure. Therefore, the enhancement coefficient H1 is raised to near 1 indicative of the maximum level (third enhancement coefficient) in such a manner that the structure can be grasped.

That is, the variance index value V included in the first range R1 and the first enhancement coefficient are associated with each other. Also, the variance index value V included in the second range R2 larger in value than the first range R1, and the second enhancement coefficient smaller than the first enhancement coefficient correspond to each other. Further, the variance index value V included in the third range R3 larger in value than the second range R2, and the third enhancement coefficient larger than the second enhancement coefficient correspond to each other.

Incidentally, now consider a balance between spatial resolution required for each region of a reconstructed image and noise.

The balance between the spatial resolution required for each region of the reconstructed image and the noise differs depending on the type of section in each region even if variances in pixel values are the same degree. For example, the noise suppression is relatively given priority in the soft part region, whereas the high spatial resolution is relatively given priority in the bone region.

In the present example, the first relation T1 is determined based on the typical pixel value C corresponding to the noted region. Therefore, the type of section in the noted region can be predicted a little from the typical pixel value C corresponding to the noted region. Such an enhancement coefficient H1 that the balance between the spatial resolution and noise suitable for the noted region is obtained can be derived from the degree of variances in pixel values in the neighborhood of the noted region in the form suitable for the predicted section.

Thus, the balance between the spatial resolution and noise suitable for the noted region can meet a complicated and delicate request that occurs due to the combination of the type of section and the variances in pixel values.

At step S6, the second relation determination part 6051 determines a second relation T2 indicative of the relationship between the typical pixel value C and enhancement coefficient H2 corresponding to the noted region according to a reconstruction function used in the image reconstruction.

At step S7, the second coefficient specifying part 6052 specifies an enhancement coefficient H2 corresponding to the typical pixel value C acquired at step S2 by referring to the second relation T2 determined at step S6.

Incidentally, as the method of determining the second relation T2, there can be considered, for example, a method of storing candidates for the second relation T2 in correspondence with one another respectively every type of reconstruction function and specifying the second relation T2 that is a candidate corresponding to a reconstruction function actually used in the image reconstruction of the X-ray CT image G.

Figure 6:
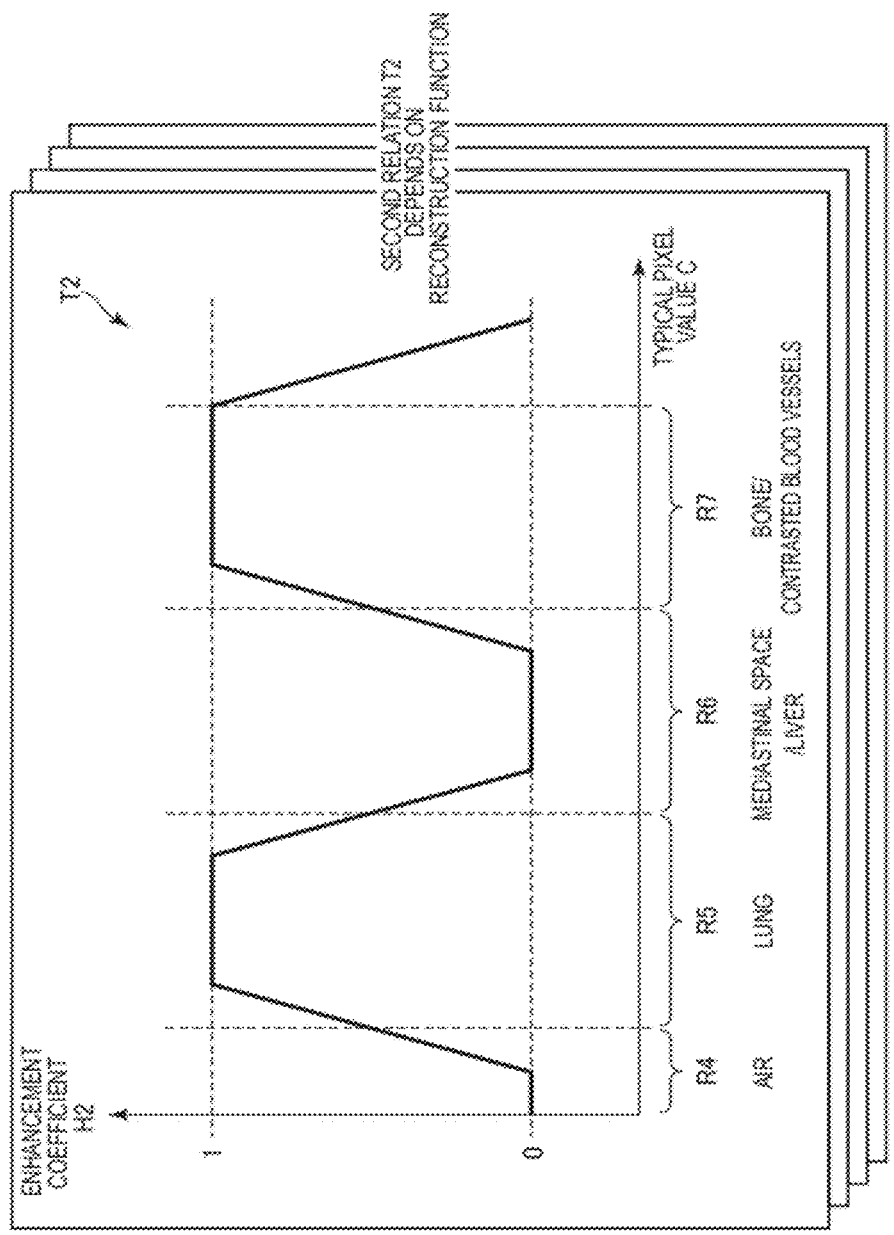
FIG. 6 is a diagram illustrating one example of a second relation indicative of a correlation between a typical pixel value in a noted region and an enhancement coefficient.

One example of the second relation is shown in FIG. 6.

When the typical pixel value C corresponding to the noted region is within a fourth range R4 smallest in the value in the second relation T2 according to this example as shown in FIG. 6, there is a high possibility that the noted region will be air. Therefore, the enhancement coefficient H2 is lowered to near 0 corresponding to the minimum level (fourth enhancement coefficient) so as to prevent noise from increasing. When the typical pixel value C corresponding to the noted region is within a fifth range R5 small in the value next, there is a high possibility that the noted region will be a lung. Therefore, the enhancement coefficient H2 is raised up to near 1 corresponding to the maximum level (fifth enhancement coefficient) in such a manner that micro points of calcification or the like can be grasped. When the typical pixel value C corresponding to the noted region is within a sixth range R6 small in the value next, there is a high possibility that the noted region will be mediastinal space, liver or the like. Therefore, the enhancement coefficient H2 is lowered to near 0 corresponding to the minimum level (sixth enhancement coefficient) so as to prevent noise from increasing. When the typical pixel value C corresponding to the noted region is within a seventh range R7 small in the value next, there is a high possibility that the noted region will be bones, contrasted blood vessels or the like. Therefore, the enhancement coefficient H2 is raised up to near 1 corresponding to the maximum level (seventh enhancement coefficient) in such a manner that a fine structure such as auditory ossicles, calcification in blood vessels or the like can be grasped.

That is, the pixel value included in the fourth range R4 and the fourth enhancement coefficient correspond to each other. The pixel value included in the fifth range R5 larger in pixel value than the fourth range R4 and the fifth enhancement coefficient larger than the fourth enhancement coefficient are associated with each other. The pixel value included in the sixth range R6 larger than the fifth range R5 in pixel value, and the sixth enhancement coefficient smaller than the fifth enhancement coefficient correspond to each other. The pixel value included in the seventh range R7 larger than the sixth range R6 in pixel value, and the seventh enhancement coefficient larger than the sixth enhancement coefficient correspond to each other.

Incidentally, the states of the spatial resolution and noise in the reconstructed image differ greatly according to the reconstruction function used in the image reconstruction. Since the second relation T2 is changed depending on the reconstruction function used in the image reconstruction in the present example, the second relation T2 to be referred can be determined in consideration of the difference in the state therebetween.

At step S8, the edge detector 606 performs edge detection processing in the noted region and its adjacent region.

At step S9, the third enhancement coefficient determination unit 607 determines an enhancement coefficient H3 in such a manner that its value becomes larger where no edge is detected rather than where the edge is detected by the edge detection processing.

It is thus possible to derive the enhancement coefficient H3 capable of preventing the occurrence of overshoot or undershoot due to the excessive enhancement of an edge portion at which the pixel value changes suddenly.

Figure 7:
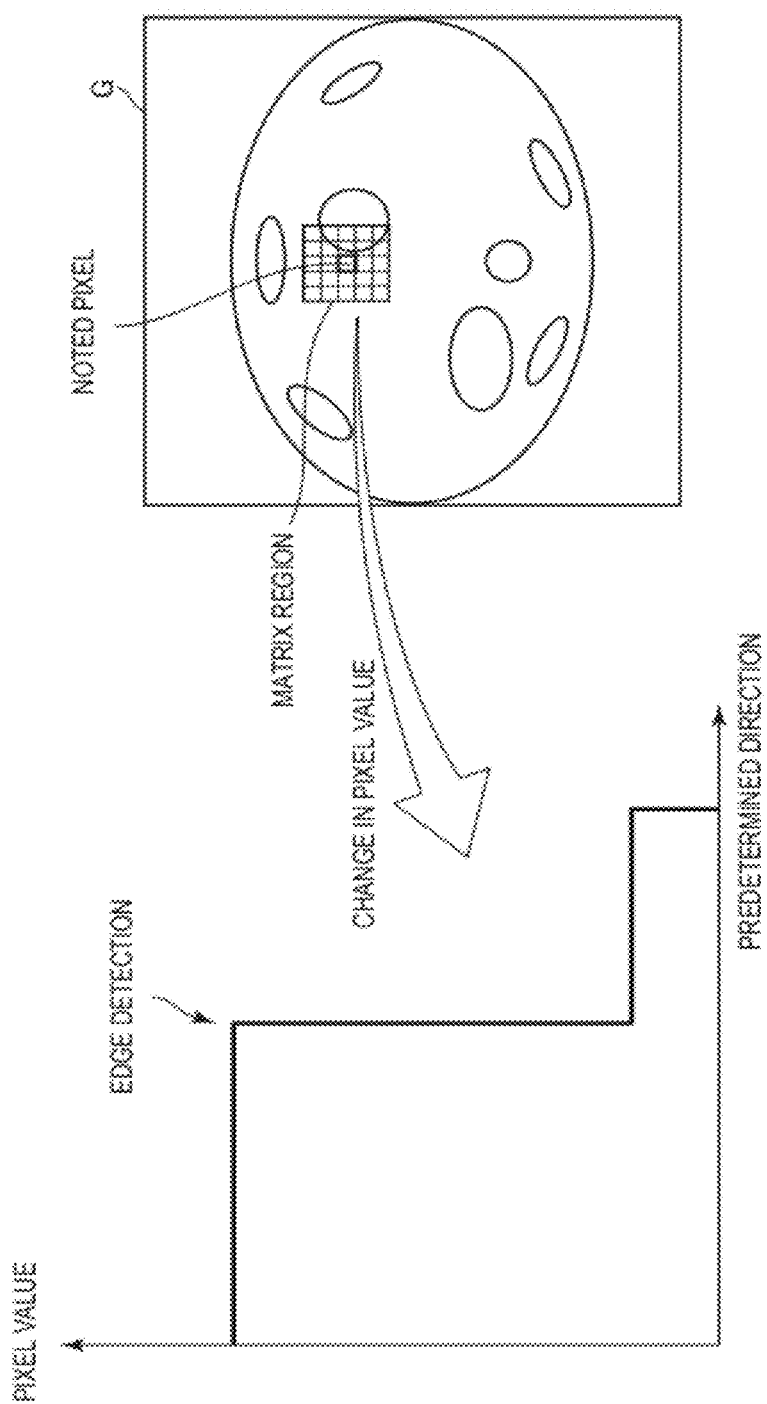
FIG. 7 shows one example of edge detection processing.

One example of the edge detection processing is shown in FIG. 7. As the edge detection processing, there is considered as shown in FIG. 7, for example, a process for, when a change in pixel value in a predetermined direction is viewed in a predetermined matrix region centering on a noted pixel, e.g., a region of 5×5 pixels, determining an edge to have been detected if the difference in pixel value between adjacent pixels is greater than or equal to a predetermined threshold value. There is considered, for example, a process for determining an edge to have been detected when the number of pixels, at which the difference in pixel value with respect to the noted pixel is greater than or equal to the predetermined threshold value, of the pixels included in the predetermined matrix region centering on the noted pixel is greater than or equal to a predetermined number.

At step S10, the distance measurement unit 608 measures a distance D from the reconstruction center, i.e., iso-center in the reconstructed image to the noted region.

At step S11, the fourth enhancement coefficient determination unit 609 determines an enhancement coefficient H4 in such a manner that its value becomes large as the distance D measured at step S10 increases.

Figure 8:
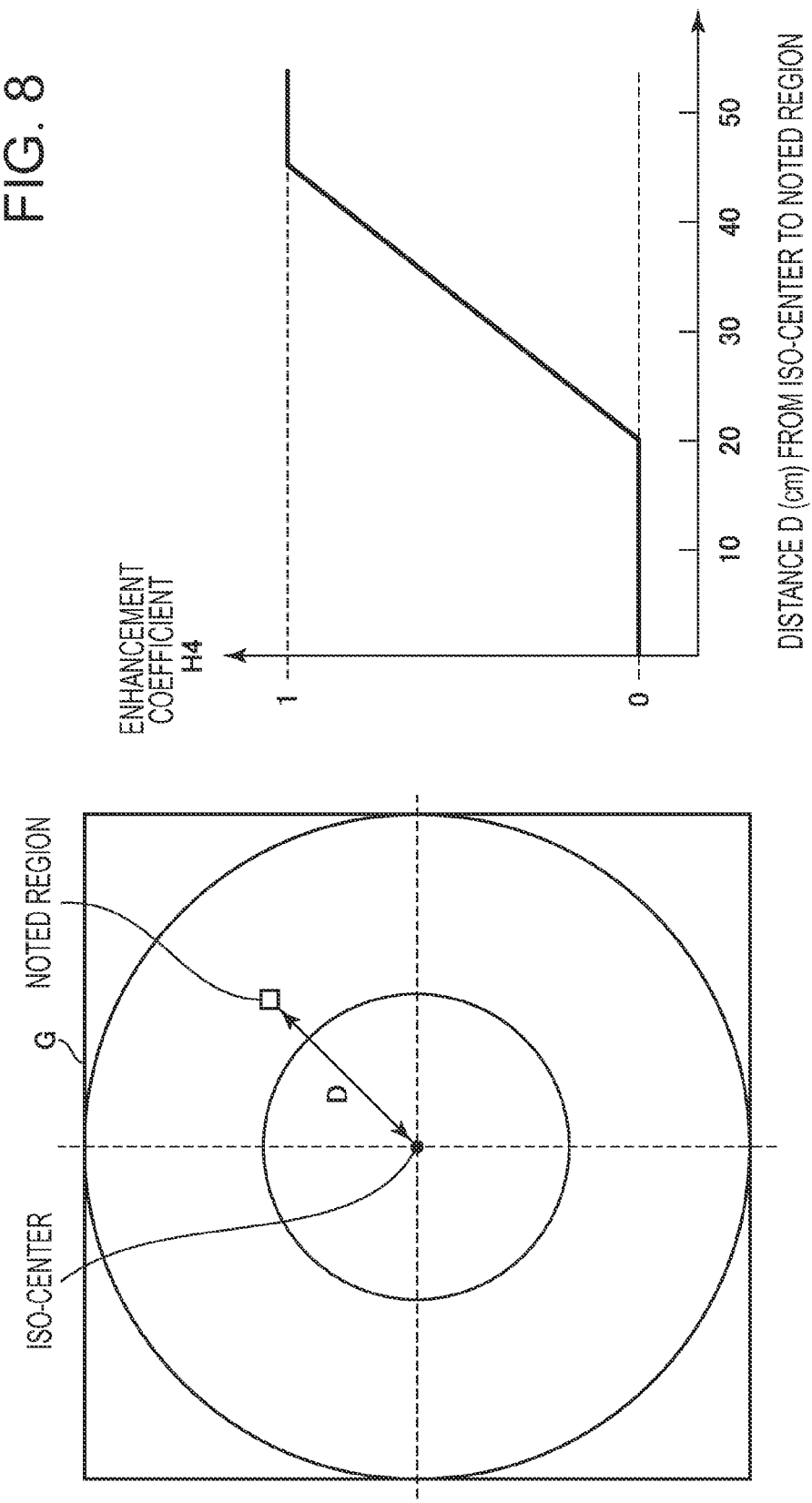
FIG. 8 is a diagram showing one example of a correlation between the distance from an iso-center to a noted region and an enhancement coefficient.

One example of the relationship between the distance D from the iso-center to the noted region and the enhancement coefficient H4 is shown in FIG. 8. In this example, the enhancement coefficient H4 is 0 in a range in which the distance D is from 0 cm to 20 cm. The enhancement coefficient H4 increases gradually in a range in which the distance D is from 20 cm to 45 cm. The enhancement coefficient H4 becomes 1 when the distance D is greater than 45 cm.

It is known that the spatial resolution becomes low with distance from the iso-center in the X-ray CT image corresponding to the reconstructed image. It is thus possible to derive an enhancement coefficient capable of suppressing a reduction in the spatial resolution at the peripheral portion of the reconstructed image.

At step S12, the enhancement degree determination part 6101 performs multiplication, addition or weighted addition or the like on all the determined enhancement coefficients H1 through H4 to thereby determine an enhancement degree HA.

At step S13, high-frequency enhancement processing is performed on the noted region, based on the enhancement degree HA determined at step S12.

As the high-frequency enhancement processing, there can be considered, for example, sharpening filter processing using a weighted coefficient matrix, which is known to date.

Thus, the high-frequency enhancement processing on which the effect of correcting the spatial resolution and noise held in each enhancement coefficient is reflected is performed on the noted region.

At step S14, the controller 613 determines whether or not a region to be set as the noted region lies elsewhere. If it exists elsewhere, the flowchart returns to step S2, where a new noted region is set and the processing is continued. If it does not exist elsewhere, the processing is terminated.

Figure 9:
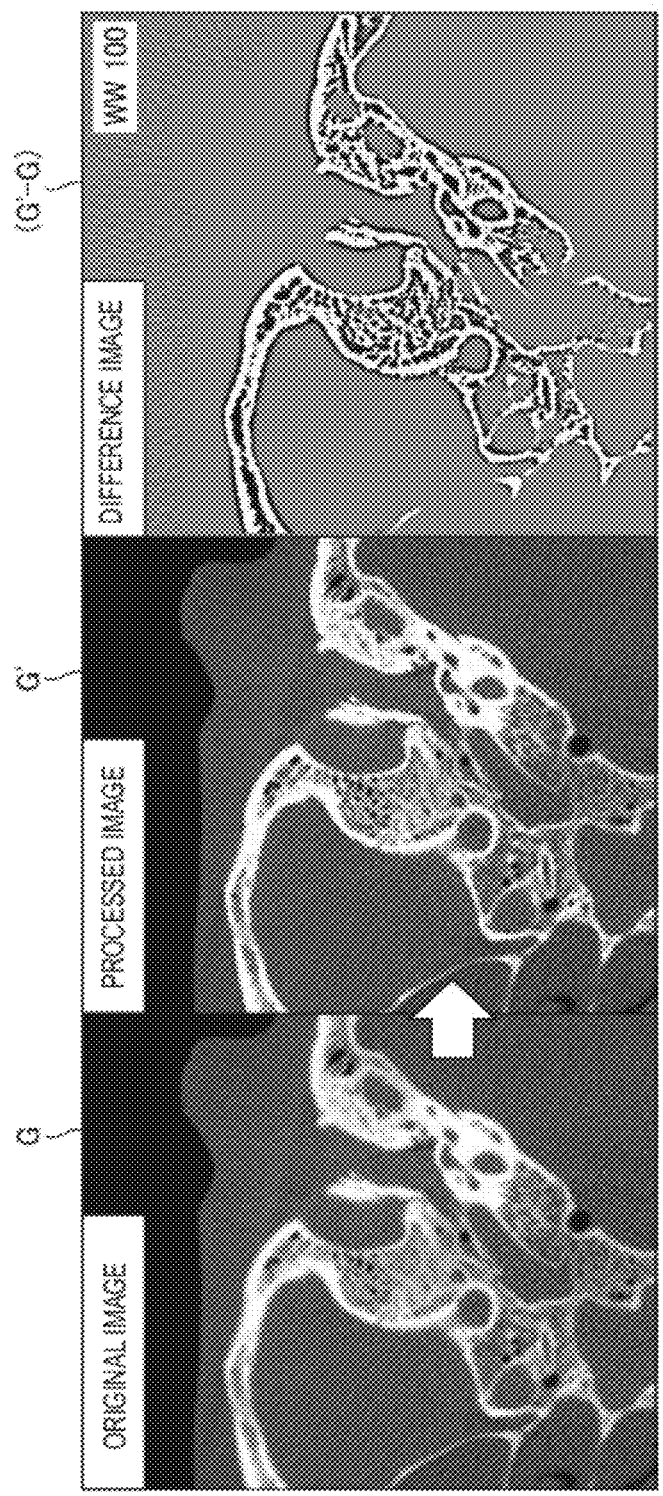
FIG. 9 is a diagram illustrating a sample image taken when the adaptive high-frequency enhancement processing is applied to an X-ray CT image of auditory ossicles.

FIG. 9 shows a sample image taken when the adaptive high-frequency enhancement processing is applied to an X-ray CT image of auditory ossicles. The left image is an original image G, the central image is a processed image G', and the right image is a difference image (G'-G) between the processed image and the original image. In the processed image G', the enhancement of high-frequency components is sufficiently performed on a high contrast region for the bones so that high spatial resolution is obtained. It is however found that the enhancement of high-frequency components is hardly performed on a soft part region and a region having a relatively flat structure of a bone part and hence an increase in noise is suppressed.

According to the embodiments described herein, the enhancement degree of the high-frequency enhancement processing performed on the noted region can be changed according to the combined condition of both the pixel value related to the noted region and the degree of variance in the pixel value.

Therefore, the type of section in the noted region and the state of its structure can first be discriminated in pieces. For example, the fine discrimination of a fine structure of each of the soft part region and the bone/contrasted blood vessels, a structure relatively flat, a structure like an artifact, etc. can be performed on the noted region in addition to the discrimination of air, lungs and the like.

It is possible to perform the high-frequency enhancement processing on the noted region with the suitable enhancement degree corresponding to the result of discrimination. For example, when it is considered that the noted region is a bone region judging from each pixel value but has a relatively flat structure judging from the degree of variances in pixel values, it is possible to suppress an increase in noise without the enhancement of the high-frequency components. Further, for example, even when the degree of variances in pixel values in a region considered to be an artifact changes depending on the type of substance or section, it is also possible to accurately determine whether the noted region is an artifact region and suppress an increase in noise without the enhancement of each high-frequency component if it is found to be the artifact region.

As a result, it is possible to suppress an increase in unnecessary noise without the enhancement of each high-frequency component with respect to a region in which noise suppression should be given priority and, in the mean time, to improve spatial resolution while enhancing each high-frequency component with respect to a region really desirous of high spatial resolution.

The embodiments described herein enable a delicate correction that cannot be obtained by the conventional method. For example, even if an enhancement coefficient determined according to only a pixel value and an enhancement coefficient determined according to only a variance index value of a pixel value are combined together to generate a new enhancement coefficient, enhancement coefficients respectively determined in another aspect may repel each other. It is difficult to perform such a delicate correction as described above.

Incidentally, the present invention is not limited to the embodiments specifically described herein, but may be added and modified in various ways within the scope not departing from the gist thereof.

For example, the combination and order of the processes for determining the enhancement coefficient are not limited to the embodiments described herein. A process based on several aspects may be omitted, a process based on another aspect may be added, and the order may be changed. The concrete contents of the process for determining the enhancement coefficient are not limited to the embodiments described herein.

Although in the embodiments described herein, for example, the respective enhancement coefficients are integrated to determine one enhancement degree, and the high-frequency enhancement processing is performed based on the enhancement degree, the high-frequency enhancement processing based on the enhancement coefficients may sequentially be performed for every enhancement coefficient.

An image processing apparatus having a functional block related to the above image processing, a program for causing a computer to function as such an image processing apparatus, and another image diagnostic apparatus equipped with such an image processing apparatus are merely exemplary. The image diagnostic could include, for example, a PET-CT apparatus, an Angio-CT apparatus, radiation therapy equipment with a CT function, etc.

The invention claimed is:

1. An image processing apparatus comprising a central processing unit programmed to:
   acquire a typical pixel value corresponding to a noted region in an image;
   calculate index values of variances in pixel values in the noted region or in both the noted region and a region adjacent to the noted region;
   determine an enhancement degree according to the acquired typical pixel value and each of the calculated index values, wherein the enhancement degree is determined based on a first relation between each of the index values and the enhancement degree, wherein possible values for the typical pixel value are divided into a plurality of ranges based on sections of a subject, and wherein the first relation is different for each of the plurality of ranges such that a first relation for a first range of the plurality of ranges applied to an index value is different from a first relation for a second range of the plurality of ranges that would be applied to the same index value; and
   perform high-frequency enhancement processing on the noted region, based on the determined enhancement degree.

2. The image processing apparatus according to claim 1, wherein in the first relation, each of the index values of the variances included in a first range are associated with a first enhancement degree, each of the index values of the variances included in a second range that is larger in index value than the first range are associated with a second enhancement degree that is smaller than the first enhancement degree, and each of the index values of the variances included in a third range that is larger in index value than the second range are associated with a third enhancement degree that is larger than the second enhancement degree.

3. The image processing apparatus according to claim 2, wherein the second range is a range of index values of variances corresponding to the existence of an artifact.

4. The image processing apparatus according to claim 1, wherein the central processing unit is further programmed to:
determine an additional enhancement degree according to the acquired typical pixel value; and
perform high-frequency enhancement processing on the noted region, based on the determined additional enhancement degree.

5. The image processing apparatus according to claim 4, wherein the central processing unit is further programmed to specify the additional enhancement degree based on a second relation between the typical pixel value corresponding to the noted region and the additional enhancement degree.

6. The image processing apparatus according to claim 5, wherein in the second relation, a typical pixel value included in a fourth range is associated with a fourth enhancement degree, a typical pixel value included in a fifth range that is larger in pixel value than the fourth range is associated with a fifth enhancement degree that is larger than the fourth enhancement degree, a typical pixel value included in a sixth range that is larger in pixel value than the fifth range is associated with a sixth enhancement degree that is smaller than the fifth enhancement degree, and a typical pixel value included in a seventh range that is larger in pixel value than the sixth range is associated with a seventh enhancement degree that is larger than the sixth enhancement degree.

7. The image processing apparatus according to claim 6, wherein the fourth range is a range of pixel values corresponding to the existence of air, and the sixth range is a range of pixel values corresponding to the existence of a soft tissue.

8. The image processing apparatus according to claim 4, wherein the central processing unit is further programmed to perform high-frequency enhancement processing on the noted region based on one of multiplication, addition, and weighted addition of a plurality of the enhancement degrees determined.

9. The image processing apparatus according to claim 5, wherein the image is an X-ray CT image, and
wherein the central processing unit is further programmed to determine the additional enhancement degree, based on the second relation, wherein the second relation is based on a reconstruction function used in reconstruction of the X-ray CT image.

10. The image processing apparatus according to claim 1, wherein the central processing unit is further programmed to:
determine an additional enhancement degree such that a larger value is acquired when an edge is not detected by edge detection processing on the noted region or the noted region and a region adjacent to the noted region, and a smaller value is acquired when the edge is detected by the edge detection processing; and
perform high-frequency enhancement processing on the noted region, based on the determined additional enhancement degree.

11. The image processing apparatus according to claim 10, wherein the edge detection processing is a process configured to:
identify a number of pixels in regions adjacent to the noted region that have a difference between their respective pixel values and a typical pixel value corresponding to the noted region that is greater than or equal to a predetermined threshold difference; and
detect an edge when the identified number of pixels is greater than or equal to a predetermined number.

12. The image processing apparatus according to claim 1, wherein the image is an X-ray CT image,
wherein the central processing unit is further programmed to:
determine an additional enhancement degree such that larger values are acquired as the distance from a center of reconstruction of the X-ray CT image to the noted region increases; and
perform high-frequency enhancement processing on the noted region, based on the determined additional enhancement degree.

13. The image processing apparatus according to claim 1, wherein the high-frequency enhancement processing is sharpening filter processing.

14. The image processing apparatus according to claim 1, wherein the typical pixel value corresponding to the noted region is one of a pixel value of a central pixel in the noted region, an average value of pixel values in the noted region or both the noted region and the adjacent region, or a weighted average value of the pixel value of the central pixel and the average value.

15. The image processing apparatus according to claim 1, wherein each of the index values of the variances is a one of a variance and standard deviation of pixel values in the noted region or pixel values in the noted region and the adjacent region.

16. An image diagnostic apparatus comprising:
an imaging apparatus configured to reconstruct an image of a subject; and
a central processing unit programmed to:
acquire a typical pixel value corresponding to a noted region in the image;
calculate index values of variances in pixel values in the noted region or in both the noted region and a region adjacent to the noted region;
determine an enhancement degree according to the acquired typical pixel value and each of the calculated index values, wherein the enhancement degree is determined based on a first relation between each of the index values and the enhancement degree, wherein possible values for the typical pixel value are divided into a plurality of ranges based on sections of the subject, and wherein the first relation is different for each of the plurality of ranges such that a first relation for a first range of the plurality of ranges applied to an index value is different from a first relation for a second range of the plurality of ranges that would be applied to the same index value; and
perform high-frequency enhancement processing on the noted region, based on the determined enhancement degree.

17. The image diagnostic apparatus according to claim 16, wherein the imaging apparatus is configured to conduct X-ray CT imaging to reconstruct the image.

18. A method for processing adaptive high-frequency enhancement using a computer, said method comprising:

acquiring, by the computer, a typical pixel value corresponding to a noted region in an image;

calculating, by the computer, index values of variances in pixel values in the noted region or in both the noted region and a region adjacent to the noted region;

determining, by the computer, an enhancement degree according to the acquired typical pixel value and each of the calculated index values, wherein the enhancement degree is determined based on a first relation between each of the index values and the enhancement degree, wherein possible values for the typical pixel value are divided into a plurality of ranges based on sections of a subject, and wherein the first relation is different for each of the plurality of ranges such that a first relation for a first range of the plurality of ranges applied to an index value is different from a first relation for a second range of the plurality of ranges that would be applied to the same index value; and performing, by the computer, high-frequency enhancement processing on the noted region, based on the determined enhancement degree.

\* \* \* \* \*